United States Patent
Ekins

(10) Patent No.: US 6,316,186 B1
(45) Date of Patent: *Nov. 13, 2001

(54) BINDING ASSAY USING BINDING AGENTS WITH TAIL GROUPS

(75) Inventor: Roger Philip Ekins, London (GB)

(73) Assignee: Multilyte Limited, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/700,530

(22) PCT Filed: Mar. 10, 1995

(86) PCT No.: PCT/GB95/00521

§ 371 Date: Oct. 23, 1996

§ 102(e) Date: Oct. 23, 1996

(87) PCT Pub. No.: WO95/24649

PCT Pub. Date: Sep. 14, 1995

(30) Foreign Application Priority Data

Mar. 11, 1994 (GB) .................................................. 9404709

(51) Int. Cl.⁷ ..................................................... C12Q 1/68

(52) U.S. Cl. ................................ 435/6; 435/7.1; 436/518; 436/532; 530/391.1; 530/387.3

(58) Field of Search ......................... 435/6, 7.1; 436/518, 436/532; 530/391.1, 387.3

(56) References Cited

U.S. PATENT DOCUMENTS 5,143,854 * 9/1992 Pirrung et al. ........................ 436/518
5,252,743 * 10/1993 Barrett et al. .
5,646,001 * 7/1997 Terstappen et al. ................. 435/7.21

FOREIGN PATENT DOCUMENTS 422861   4/1991 (EP) .
WO8401031   3/1984 (WO) .

OTHER PUBLICATIONS

Berson and Yalow, "Methods in Investigative and Diagnostic Endocrinology", pp. 111–116 (1973).

R.P. Viscidi et al., Journal of Clinical Microbiology, 27: 120–125 (1989).

R. Elkins, Nuclear Medicine and Biology, 21: 495–521 (1994).

Scouten et al; "Reversible Immobilization of Antibodies on Magnetic Beads," Analytical Biochem 205: 313–318 (1992).*

Syvanen et al. 1986 Nucleic Acids Research 14 (12) pp. 5037–5048.*

* cited by examiner

Primary Examiner—Michael P. Woodward
Assistant Examiner—Mary K. Zeman
(74) Attorney, Agent, or Firm—Dann Dorfman Herrell and Skillman, P.C.

(57) ABSTRACT

The present invention discloses methods and kits for the determination of the concentration of one or more analytes in a liquid sample using capture agents immobilized on a solid support and binding agents for binding the analyte(s), the binding agents having tail groups capable of binding to the respective capture agent. Preferably, the capture agents and binding agents are complementary oligonucleotides, and the capture agents are immobilized in the form of microspots. The use of the tail groups and capture agents can allow the binding of the analyte(s) to the binding agent(s) to take place in solution, rather than at a surface, improving the kinetics associated with this process. In addition, the user of the assay can customize any suitable binding agents for use with a universal support, by attaching tail groups to them.

15 Claims, 3 Drawing Sheets

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
    Oligonucleotide

<400> SEQUENCE: 1
cacacacaca cacacaca                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
    Oligonucleotide

<400> SEQUENCE: 2
gtgtgtgtgt gtgtgtgt                                                    18

<210> SEQ ID NO 3

```
-continued

<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
gagagagaga gagagaga                                              18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ctctctctct ctctctct                                              18
```

BINDING ASSAY USING BINDING AGENTS WITH TAIL GROUPS

FIELD OF THE INVENTION

The present invention relates to binding assays using binding agents with tail groups, and in particular binding agents having oligonucleotide tail groups. These binding assays are useful in determining the concentration of analytes in liquid samples.

BACKGROUND OF THE INVENTION

It is known to measure the concentration of an analyte, such as a drug or hormone, in a liquid sample by contacting the liquid sample with a binding agent immobilised on a solid support, the binding agent having binding sites specific for the analyte, separating the binding agent having analyte bound to it and measuring a value representative of the fraction of the binding sites of the binding agent that are occupied by the analyte. Typically, the concentration of the analyte in the liquid sample can then be determined by comparing the value representative of the fraction of the binding sites occupied by analyte against values obtained from a series of standard solutions containing known concentrations of analyte.

In the past, the measurement of the fraction of the binding sites occupied has usually been carried out by back-titration with a labelled developing reagent using either so-called competitive or non-competitive methods.

In the competitive method, the binding agent having analyte bound to it is back-titrated, either simultaneously or sequentially, with a labelled developing agent, which is typically a labelled version of the analyte or an anti-idiotypic antibody capable of recognising empty binding sites of the binding agent. The developing agent can be said to compete for the binding sites on the binding agent with the analyte whose concentration is being measured.

The fraction of the binding sites which become occupied with the labelled analyte can then be related to the concentration of the analyte as described above.

In the non-competitive method, the binding agent having analyte bound to it is back-titrated with a labelled developing agent capable of binding to either the bound analyte or to the occupied binding sites on the binding agent. The fraction of the binding sites occupied by analyte can then be measured by detecting the presence of the labelled developing agent and, just as with competitive assays, related to the concentration of the analyte in the liquid sample as described above.

In both competitive and non-competitive methods, the developing agent is labelled with a marker to allow the developing agent to be detected. A variety of markers have been used in the past, for example radioactive isotopes, enzymes, chemiluminescent markers and fluorescent markers.

In the field of immunoassay, competitive assays have in general been carried out in accordance with design principles enunciated by Berson and Yalow, for instance in "Methods in Investigative and Diagnostic Endocrinology" (1973), pages 111–116. Berson and Yalow proposed that in the performance of competitive immunoassays, maximum sensitivity is achieved when an amount of binding agent is used to bind approximately 30–50% of a low concentration of the analyte to be detected. In non-competitive immunoassays, maximum sensitivity is generally thought to be achieved by using sufficient binding agent to bind close to 100% of the analyte in the liquid sample. However, in both cases immunoassays designed in accordance with these widely-accepted precepts require the volume of the sample to be known and the amount of binding agent used to be accurately known or known to be constant.

In International Patent Application WO 84/01031, I disclosed that the concentration of an analyte in a liquid sample can be measured by contacting the liquid sample with a small amount of binding agent having binding sites specific for the analyte. In this "ambient analyte" method, provided the amount of binding agent is small enough to have only an insignificant effect on the concentration of the analyte in the liquid sample, it is found that the fraction of the binding sites on the binding agent occupied by the analyte is effectively independent of the volume of the sample.

This approach is further refined in EP 304,202 which discloses that the sensitivity and ease of development in the assays in WO 84/01031 are improved by using an amount of binding agent less than $0.1V/K$ moles located on a small area (or "microspot") on a solid support, where V is the violume of the sample and K is the affinity constant of the binding agent for the analyte. In both of these references, the fraction of the binding sites occupied by the analyte is measured using either a competitive or non-competitive technique as described above.

SUMMARY OF THE INVENTION

There is continuing need to develop binding assays which have enhanced kinetics to allow assays to be carried out more quickly and easily. In addition, it would be desirable to provide a binding assay which the user of the assay can easily customise for the detection of different groups of analytes.

Accordingly, in a first aspect, the present invention provides a method of determining the concentrations of analytes in a liquid sample comprising:

(a) immobilising one or more capture agents on a solid support, each capture agent being capable of specifically binding a given binding agent;

(b) contacting the liquid sample with one or more binding agents, each binding agent having binding sites specific for a given analyte so that a fraction of the binding sites become occupied by the analyte, and a tail group adapted to bind to a corresponding capture agent;

(c) contacting the liquid sample, either simultaneously or sequentially with the step (b), with the immobilised capture agents so that the binding agents become bound to their respective capture agents; and (d) determining the fraction of the binding sites of a binding agent occupied by analyte to determine the concentration of the analyte in the liquid samples.

Accordingly, the present invention provides an assay in which the binding of the analytes takes place in the liquid phase, rather than at a surface of a solid substrate. This enhances the kinetics of the reaction between analyte and binding agent.

Thus, in one embodiment, contacting the liquid sample with the binding and capture agents simultaneously allows the assay to be carried out in a single step, eg using a single reaction vessel. Alternatively, sequential contact of the binding agent(s), and capture agent(s) may be preferred, especially where the liquid is serum or blood, and non-specific binding is an important source of error. In these cases, the binding agent can be first contacted with the liquid sample in a first vessel and then the sample transferred to a second vessel to allow the capture agent to bind the binding agent to the solid support.

In a second aspect, the present invention provides a method of immobilising one or more binding agents on a support, each binding agent having binding sites specific for a given analyte and a tail group adapted to bind to a capture agent, comprising:
  (a) immobilising one or more capture agents on a support each capture agent being capable of binding to the tail group of a given binding agent and,
  (b) contacting the binding agents with the support having the capture agents immobilised thereon so that the binding agents become specifically bound to their respective capture agents through their tail groups.

The above method can additionally comprise the step of attaching the tail groups to the binding agents prior to exposing them to the capture agents immobilised on the support.

Thus, it is possible for the user of the assay to customise binding agents for use in determining the concentration of different groups of analytes and using the customised binding agents in conjunction with a universal support having capture agents immobilised on it, to which the binding agents can individually bind by virtue of their tail groups.

In this aspect of the invention, the assay is carried out by exposing the support to a liquid sample after the binding agent(s) has or have become bound to the capture agent(s).

In either aspect, the present invention provides an assay in which the binding agent is indirectly linked to capture agent immobilised on the substrate via the tail group.

Preferably, the capture agent is an oligonucleotide sequence which can hybridise to a complementary sequence comprising the tail group of the binding agent. The oligonucleotides acting as capture agent or tail of the binding agent are sufficiently long to provide strong and specific hybridisation under the stringency conditions used in the assay. Typically, complementary oligonucleotides of at least about 8 or 9 nucleotides in length are used. In a preferred embodiment, the oligonucleotides are preferably between 8 and 30 bases, more preferably between 16 and 20 bases, in length. However, the use of very long polynucleotides is not preferred as these can lead to a reduction in the specificity of binding different capture agents or to self hybridise, forming hairpin loops (double stranded regions). However, a suitable length and sequence of oligonucleotide for a set of assay conditions can readily be determined by those skilled in the art.

Conveniently, the binding agent is an antibody having binding sites specific for an analyte. Accordingly, when the capture agent on the support is exposed to the liquid phase binding agent, the binding agent becomes bound to the solid support. Alternatively, where the analyte is a nucleic acid sequence, the binding agent can be an oligonucleotide. Thus, in this embodiment, the binding agent has a first sequence capable of hybridising to the analyte and a second sequence acting as the tail group.

Preferably, a small amount of binding agent is used in accordance with the assays disclosed in WO 84/01031 or EP 304,202, so that the volume of the liquid sample need not be known. Thus, the amount of binding agent should be sufficiently small so that it does not significantly affect the ambient concentration of the analyte in the liquid sample. Typically, the use of an amount of binding agent which binds less than 5% of the analyte is preferred. However, the use of a smaller amount of binding agent, eg to bind 2% or 1% of the analyte, further reduces the disturbance to the ambient concentration of the analyte and helps to minimise the error in determining the analyte concentration.

Where the assay is conducted in accordance with EP 304,202 using less than $0.1V/K$ moles of binding agent, the affinity constant (K) for the binding of analyte to binding agent is measured in accordance with normal practice. This means the value of the affinity constant used to determine how much binding agent constitutes $0.1V/K$ moles is the value that is obtained under the conditions (eg reactants, time of incubation, pH, temperature etc) that are used in the assay.

Preferably, each capture agent is used in excess to bind substantially all of a given binding agent. This maximises the assay sensitivity and ensures that when the amount of binding agent used needs to be known or known to be constant, the user of the assay can be confident that substantially all of a binding agent used in an assay becomes bound to its capture agent on the support.

Preferably, molecules of capture agent are immobilised on a support at discrete locations, eg as microspots. This allows the concentration of a plurality of different analytes to be simultaneously determined using a plurality of different capture agents at a series of locations on the support. Where the capture agent(s) is or are immobilised as microspots, the sensitivity of the assay can be improved immobilising the capture agent at high density, thereby improving the signal-to-noise ratio (see for example our co-pending application PCT/GB94/02814). Assuming sample volumes of the order of 0.1–1.0 ml, the microspots preferably have an area less than 1 mm$^2$ and a final surface density of binding agent between 1000 and 100000 molecules/$\mu$m$^2$.

Alternatively, a given capture agent can be immobilised on a support at a plurality of locations so that a series of measurements of the concentration of an analyte can be made simultaneously.

Preferably, the fraction of the binding sites occupied by the analyte is detected using developing agents in a competitive and/or non-competitive method as described above. The developing agents are capable of binding to occupied or unoccupied binding sites of the binding agent or to bound analyte and are labelled to enable bound developing agent to be detected. Preferably, the developing agents are labelled antibodies.

The markers can be radioactive isotopes, enzymes, chemiluminescent markers or fluorescent markers. The use of fluorescent dye markers is especially preferred as the fluorescent dyes can be selected to provide fluorescence of an appropriate colour range (excitation and emission wavelength) for detection. Fluorescent dyes include coumarin, fluorescein, rhodamine and Texas Red. Fluorescent dye molecules having prolonged fluorescent periods can be used, thereby allowing time-resolved fluorescence to be used to measure the strength of the fluorescent signal after background fluorescence has decayed. Latex microspheres containing fluorescent or other markers, or bearing them on their surface can also be employed in this context. The signals from the markers can be measured using a laser scanning confocal microscope.

Alternatively, other high specific activity labels such as chemiluminescent labels can be used. In the case of chemiluminescent labels, the signals from different chemiluminiscent labels used to mark binding agent or developing agent can be simultaneously detected using, for example a charge-coupled device (CCD).

The binding agent (or a proportion of it) can conveniently be labelled, eg with a fluorophor. In accordance with the method set out in EP 271,974, this means that it is not necessary for the user of the assay to know the amount of binding agent or to know that it is constant. This is because the ratio of the signals from the binding agent and the signal indicating the fraction of the binding sites of the binding agent occupied by analyte is dependent on the fraction of the sites of the binding agent occupied by the analyte, but is independent of the total amount of binding agent present.

Alternatively, if the user of the assay knows the volume of the sample, a larger amount of binding agent can be used so that the assay is not operating under ambient analyte conditions. This allows the concentration of the analyte to be determined using one label on the developing agent and either knowing the amount of binding agent is constant or labelling it with a second marker so that the amount is known.

In a variant of this approach (described in our co-pending application PCT/GB94/02813), two labelled developing agents can be used, a first capable of specifically binding to unoccupied binding sites of the binding agent and a second capable of binding to occupied binding sites or bound analyte. Thus, the signal from either marker is representative of the fraction of the binding sites occupied by analyte, while the sum of the signals is representative of the total amount of binding agent used.

This method can also avoid the necessity of knowing that a constant amount of binding agent is used as variations in the amount of binding agent immobilised can readily be corrected for. Under these circumstances, the sample volume v must either be known or constant. This can be seen from the following formula show how the signals from two labelled developing agents relates to the concentration of analyte in a sample.

Let the signal emitted by the label marking the developing agent directed against occupied binding agent binding sites be given by $S_o$, and the signal emitted by the label marking the developing agent directed against unoccupied binding agent binding sites be given by $S_u$, and let the constants relating the respective signals to occupied and unoccupied sites be $\epsilon_o$ and $\epsilon_u$ respectively, and K=the effective equilibrium constant governing the reaction between the analyte and binding agent.

Then, if the analyte concentration in a sample is given by Y, $$Y=(S_o/\epsilon_o)[\epsilon_u/(KS_u)+1/v]$$

Assuming v is known, this equation contains two unknown constants, $\epsilon_o$ and $\epsilon_u/K$. By determining the signals $S_o$ and $S_u$ for a series of known analyte concentrations, these constants can be determined, and unknown analyte concentrations estimated from corresponding determinations of $S_o$ and $S_u$. Thus, the assay need not work under ambient analyte conditions.

Under ambient analyte conditions, the term $1/v$ becomes negligible, and $S_o/S_u$ is proportional to the ambient analyte concentration.

In a first kit aspect, the present invention provides a kit for determining the concentrations of one or more analytes in a liquid sample in a method as described above, the kit comprising:

(a) a solid substrate having attached thereto at a plurality of locations capture agent capable of specifically binding a binding agent;

(b) one or more binding agents, each binding agent having binding sites specific for an analyte, and a tail group adapted to bind one or more capture agents; and (c) one or more developing agents having markers capable of binding to occupied binding agent binding sites or analyte bound to binding agent or unoccupied binding agent binding sites.

In a second kit aspect, the present invention provides a kit for customising an assay for the determination of the concentration of one or more analytes comprising:

(a) one or more tail groups, each tail group being for attachment to a binding agent;

(b) a solid substrate having attached thereto at a plurality of locations one or more capture agents capable of specifically binding to a tail group;

wherein the user of the assay attaches the tail groups to the binding agents, thereby providing binding agents which can be used in conjunction with the solid substrate to which the capture agents are attached in a method as described above.

DESCRIPTION OF THE DRAWINGS

A preferred embodiment of the present invention will now be described with reference to the accompanying schematic drawings in which.

DETAILED DESCRIPTION

Figure 1:
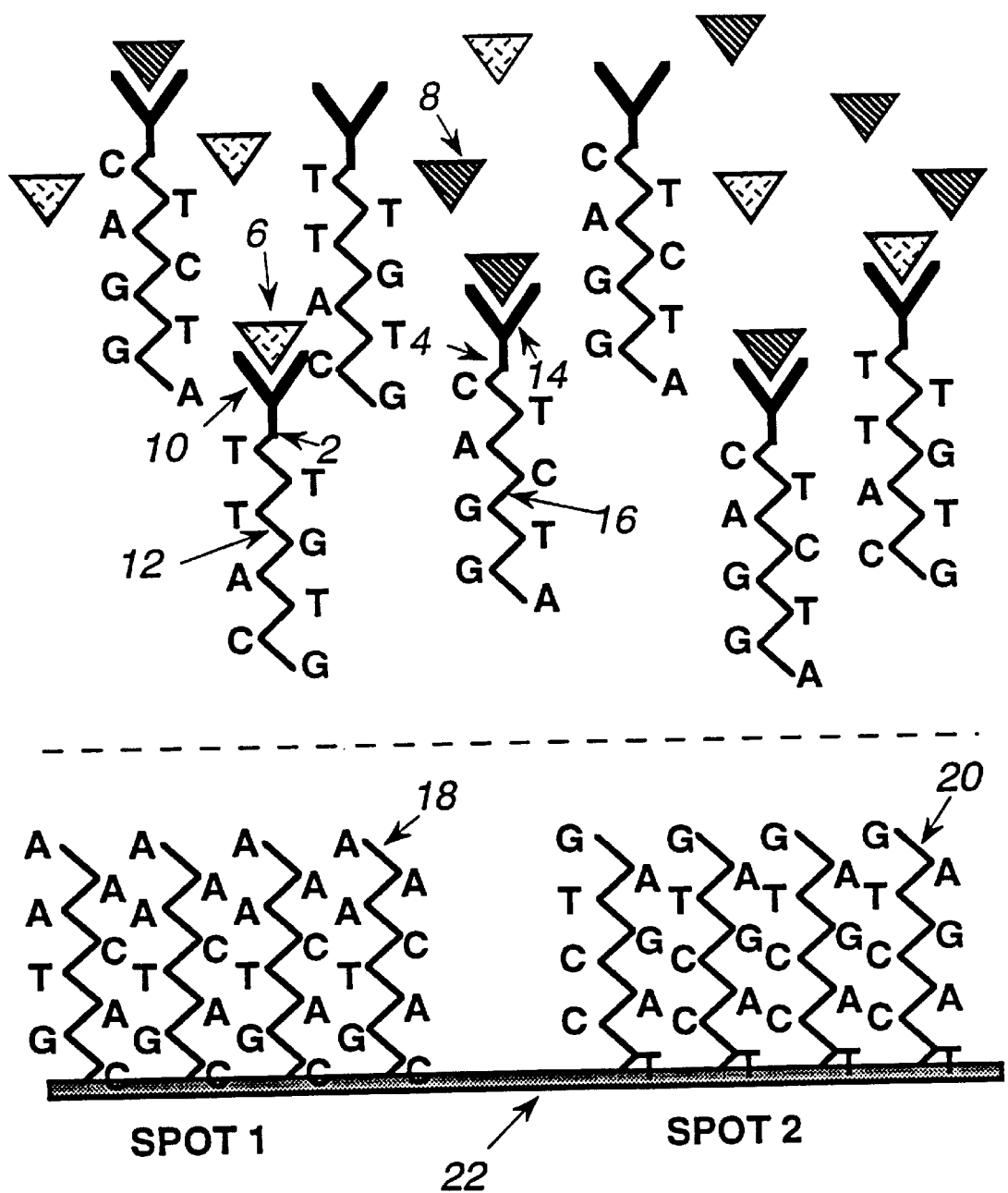
FIG. 1 shows an assay to detect two analytes in a liquid sample using two species of capture agent and two species of binding agent, the capture agent immobilised at two microspots.
Figure 2:
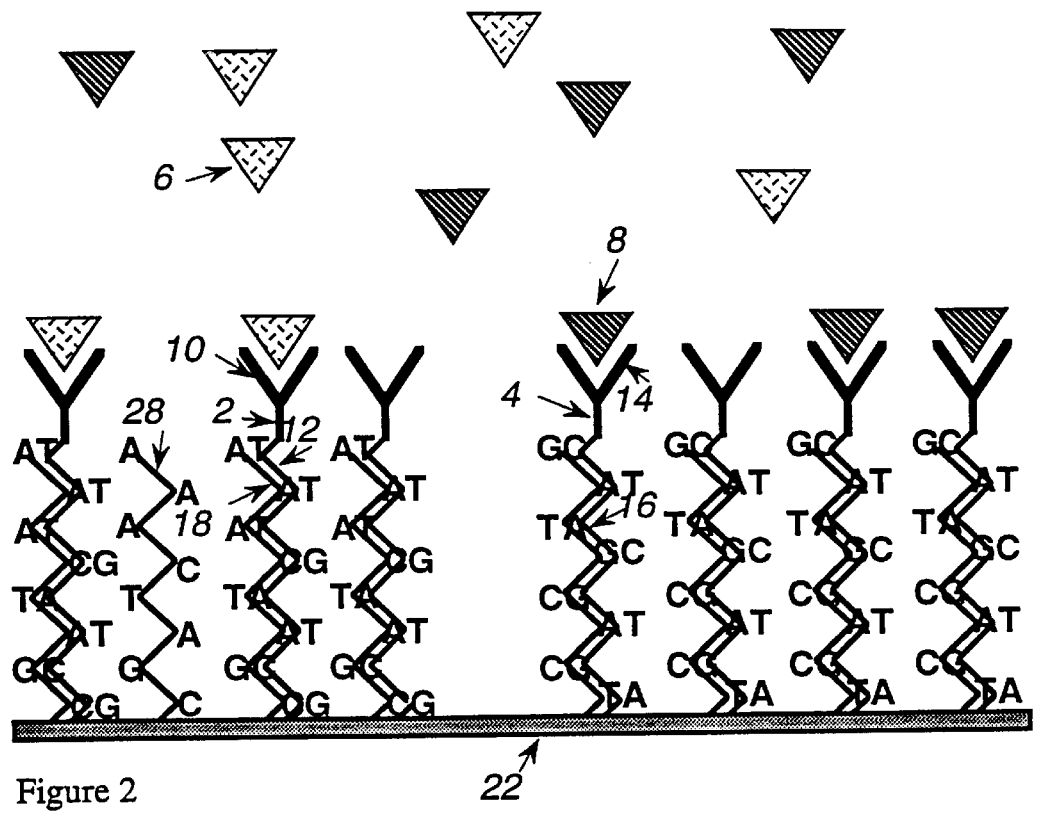
FIG. 2 shows the assay of FIG. 1 in which the capture agent has become bound to the binding agent.
Figure 3:
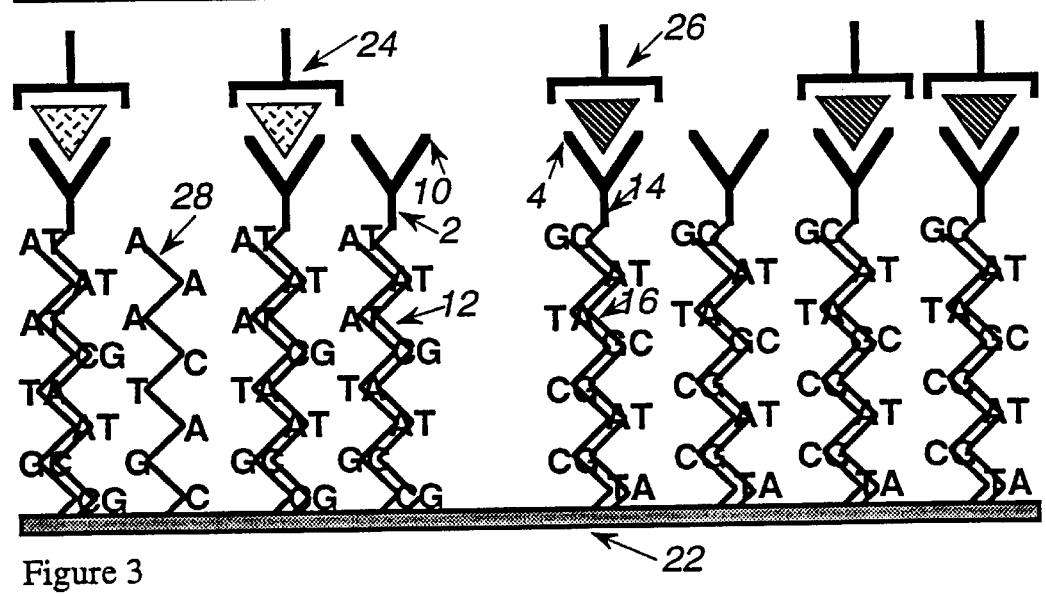
FIG. 3 shows a non-competitive method of determining the occupancy of the binding agent using a second labelled antibody; and, FIG. 4 shows a graph of signal plotted against TSH concentration from the experimental example below.

FIGS. 1 to 3 show a binding assay in which two species of binding agent 2,4 having binding sites specific for different analytes 6,8 are used. Each binding agent 2,4 comprises an antibody 10,14 provided with an oligonucleotide tail group 12,16. The oligonucleotide tail groups have different nucleotide sequences, the sequences being complementary to one of the sequences of capture agents 18,20 immobilised on a solid support 22 in the form of microspots. In this example, the oligonucleotides are 8 nucleotides long.

In the assay, the two analytes 6,8 in the sample are exposed to binding agents 2,4 so that a fraction of the analytes 6,8 become bound to the antibodies 10,14. As this reaction occurs in the liquid phase, the kinetics of the reaction between the antibodies 10,14 and the analytes (antigens) 6,8 are optimised.

Simultaneously or sequentially with the initial antibody/analyte reaction, the liquid sample and binding agent are exposed to the solid support 22 having capture agents 18,20 immobilised on it. This allows the nucleotide sequences 12,16 of the binding agents 2,4 to bind to the complementary sequences of the capture agents 18,20 immobilised on the support 22. This is shown in FIG. 2. However, the capture agents 16,18 are generally used in excess to ensure that substantially all the binding agent 10,14 is bound to the support 22. Thus, in FIGS. 2 and 3, one molecule of capture agent 28 is left unoccupied. The fraction of the binding sites of the binding agents 2,4 can then be determined using a conventional back-titration technique. Thus, in FIG. 3 labelled antibodies 24,26 are used in a non-competitive technique to mark the presence of occupied binding agents 2,4 respectively. As the antibodies 24,26 are labelled with markers (not shown) a fraction of the binding sites of the binding agents 2,4 can then be determined. This in turn allows the concentration of the analytes in the liquid sample to be found, eg by reference to results obtained using a series of solutions of known analyte concentration.

The assay shown in FIGS. 1 to 3 can be adapted to measure the concentration of any pair of analytes using the same solid support 22 having capture agents 18,20 immobilised on it. This can be done by providing binding agent suitable for binding an analyte with an oligonucleotide tail group 12,16 so that the binding agents will specifically bind to one of the microspots 18,20. Thus, it is envisaged that the user of the assay will be able to customise his or her binding agent for use with a universal array of microspots.

EXAMPLE

Reagents

1) Mouse IgG (monoclonal anti-TSH) from the Scottish Antibody Production Unit (SAPU).
2) Rabbit IgG, goat anti-mouse IgG (whole molecule) and goat anti-rabbit IgG (whole molecule) antibodies from Sigma.
3) Sulfate Fluospheres, 0.1 µm diameter, yellow/green fluorescent (ex 490; em 515 nm) and Sulfate Fluospheres, 0.1 µm diameter, red fluorescent (ex 580; em 605 nm) from Molecular Probes.
4) Oligonucleotides from Oswell DNA Service:
   a) CACACACACACACACA with 5'-biotin modification (poly-CA).
   b) GTGTGTGTGTGTGTGT with 51'-phosphorothioate modification (poly-GT)
   c) GAGAGAGAGAGAGAGA with 5'-biotin modification (poly-GA)
   d) CTCTCTCTCTCTCTCT with 5'-phosphorothioate modification (poly-CT)
5) Sulfo-LC-SPDP {sulfosuccinimidyl 6-[3'-(2-pyridyldithio)-propionamido]hexanoate} from Pierce.
6) PD10 columns and Sephadex G200 from Pharmacia.
7) RIA grade Bovine Serum Albumin (BSA), Tween20, sodium azide, di-sodium hydrogen orthophosphate anhydrous, sodium di-hydrogen orthophosphate, EDTA and Trizma from Sigma
8) Avidin DX from Vector Laboratories
9) Centricon-30 and Centriprep-30 concentrators from Amicon
10) Thyroid stimulating hormone (TSH) from NIH USA Adsorption of Anti-Mouse IgG and Anti-Rabbit IgG Antibodies to Sulfate FluoSpheres 1) A 0.5 ml aliquot of 2% (10 mg), 0.1 µm yellow/green FluoSpheres was added to 2 mg of goat anti-mouse IgG antibody dissolved in 0.5 ml 0.1 µM phosphate buffer, pH7.4. A 0.5 ml aliquot of 2% (10 mg), 0.1 µm red FluoSpheres was added to 2 mg of goat anti-rabbit IgG antibody dissolved in 0.5 ml 0.1M phosphate buffer, pH7.4. Both preparations were shaken overnight at room temperature.
2) The two preparations were centrifuged for 10 min at 8° C. in a MSE High-Spin 21 Ultra-centrifuge.
3) Each pellet was dispersed in 2 ml of 1% BSA in phosphate buffer, shaken for 1 hour at room temperature and centrifuged as above.
4) Each pellet was dispersed in 2 ml of 0.5% Tween20 in phosphate buffer, shaken for 30 min at room temperature and centrifuged as above.
5) Each pellet was dispersed in 2 ml of phosphate buffer and centrifuged as above.
6) Each pellet was dispersed in 2 ml of phosphate buffer and centrifuged as above.
7) Each pellet was dispersed in 2 ml of 1% BSA containing 0.1% sodium azide and stored at 4° C.

Conjugation of Mouse Monoclonal IgG and Rabbit IgG to Oligonucleotides 1) 3 mg of sulpho-LC-SPDP was added to 4.6 mg of mouse anti-TSH monoclonal or rabbit IgG dissolved in 1 ml of PBS/EDTA and shaken for 30 min at room temperature.
2) The activated antibodies were separated from unreacted SPDP on PD10 columns. The samples were eluted with PBS/EDTA and 0.5 ml fractions collected.
3) The fractions from the first peak containing the activated antibody were pooled and concentrated using a Centricon-30 concentrator to approximately 10 µl.
4) 100 nM of 5'-phosphorothioate modified poly-GT oligonucleotide was added to 14.8 nM of the activated mouse monoclonal IgG. 58.3 nM of 5'-phosphorothioate modified poly-CT oligonucleotide was added to 8.7 nM of the activated rabbit IgG. Both preparations were made up to 1 ml with PBS/EDTA and shaken overnight at room temperature.
5) The oligonucleotide conjugated mouse and rabbit IgG preparations were separated from unreacted oligonucleotides on a Sephadex G200 column (1.5×45 cm). The samples were eluted with PBS/EDTA and 2 ml fractions collected.
6) The fractions from the first peak containing the oligonucleotide conjugated antibody were pooled and concentrated using a Centriprep-30 concentrator to approximately 500 µl and stored at 4° C.

To Demonstrate That a Mixture of Oligonucleotide-Conjugated Antibodies Would Hybridize Only With Complementary Oligonucleotide Deposited on a Solid-Phase as Microspots 1) Dynatech black Microfluor microtitre wells were coated with 50 µl of avidin-DX in 0.1M bicarbonate buffer, pH 8.5 and at a concentration of 5 µg/ml for 5 min at room temperature.
2) After washing with 0.01M phosphate buffer, the avidin coated microtitre wells were blocked with 200 µl of 1% BSA for 1 hour at room temperature and washed again with the same buffer and dried.
3) A 0.25 µl droplet of each of the two 5'-biotin modified poly-CA and poly-GA oligonucleotides in 0.1% BSA and at a concentration of 0.025 nM/ml were deposited on opposite sides of avidin coated microtitre wells and allowed to react for 30 min under a moist atmosphere. The droplets were then aspirated and the microtitre wells washed with phosphate buffer.
4) A 50 µl aliquot of Tris-HCl assay buffer containing 0.25 µg/ml each of the poly-GT-conjugated mouse monoclonal IgG and poly-CT-conjugated rabbit IgG was added to all but the control microtitre wells (50 µl of assay buffer containing unconjugated mouse and rabbit IgG was added to the control wells instead), shaken for 1 hour under a moist atmosphere and washed with phosphate buffer containing 0.05% Tween20.
5) A 200 µl aliquot of Tris-HCl assay buffer containing 0.3 µg/ml goat anti-mouse IgG antibody conjugated yellow/green FluoSpheres and 0.6pg/ml goat anti-rabbit IgG antibody conjugated red FluoSpheres was added to all microtitre wells, shaken for 1 hour at room temperature, washed with phosphate-Tween20 buffer and scanned with a confocal laser scanning microscope equipped with an Argon/Krypton laser.

Results

Excitation: 488DF10
Emission: 525DF35

| Sample | Yellow/Green Signal |
|---|---|
| Control | 13.3 ± 0.5 |
| Avidin- - -B-Poly-CA- - -Poly-GT-Mouse IgG microspot | 100.9 ± 10.9 |
| Avidin- - -B-Poly-GA- - -Poly-CT-Rabbit IgG microspot | 16.9 ± 0.3 |

Excitation: 568DF10
Emission: 585EFLP

| Sample | Red Signal |
|---|---|
| Control | 22.0 ± 0.2 |
| Avidin- - -B-Poly-CA- - -Poly-GT-Mouse IgG microspot | 24.0 ± 0.4 |
| Avidin- - -B-Poly-GA- - -Poly-CT-Rabbit IgG microspot | 99.8 ± 2.7 |

Conclusions (1) The poly-GT oligonucleotide tagged mouse IgG hybridized only with complementary biotinylated poly-CA but not non-complementary biotinylated poly-GA oligonucleotide microspots deposited on the same microtitre well.
(2) The poly-CT oligonucleotide tagged rabbit IgG hybridized only with complementary biotinylated poly-GA but not non-complementary biotinylated poly-CA oligonucleotide microspots deposited on the same microtitre well.

To Demonstrate Antigen Binding of the Oligonucleotide Tagged Antibody Microspots 1) Dynatech black Microfluor microtitre wells were coated with 50 µl of avidin-DX in 0.1 M bicarbonate buffer, pH 8.5 and at a concentration of 5 µg/ml for 5 min at room temperature.
2) After washing with 0.01M phosphate buffer, the avidin coated microtitre wells were blocked with 200 µl of 1% BSA for 1 hour at room temperature and washed again with the same buffer and dried.
3) A 0.25 droplet of 5'-biotin modified poly-CA oligonucleotide in 0.1% BSA and at a concentration of 0.025nM/ml was deposited on each of the avidin coated microtitre wells and allowed to react for 30 min under a moist atmosphere. The droplets were then aspirated and the microtitre wells washed with phosphate buffer.
4) A 50 µl aliquot of Tris-HCI assay buffer containing 0.25 µg/ml of the poly-GT-conjugated anti-TSH mouse monoclonal IgG was added to the microtitre wells, shaken for 1 hour under a moist atmosphere and washed with phosphate buffer containing 0.05% Tween2.
5) A 200 µl aliquot of TSH standards in Tris-HCI assay buffer (0, 0.1, 0.3 & 1.0 µU/ml) was added to triplicate wells and incubated for 1 hour at room temperature and washed with phosphate-Tween20 buffer.
6) A 200 µl aliquot of 50 µg/ml anti-TSH developing antibody conjugated yellow/green sulfate FluoSpheres was added to all microtitre wells, shaken for 1 hour at room temperature, washed with phosphate-Tween20 buffer and scanned with a confocal laser scanning microscope equipped with an Argon/Krypton laser.

RESULTS AND CONCLUSION

Figure 4:
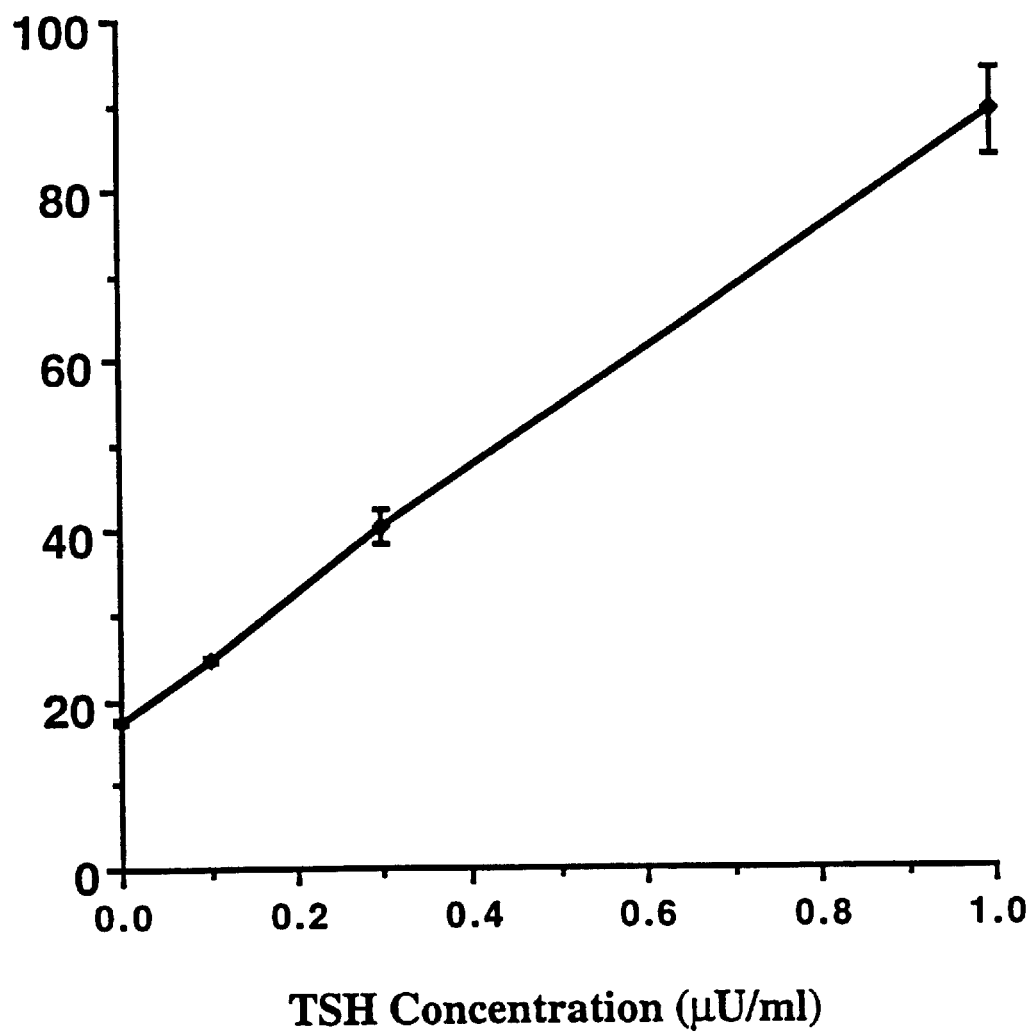

The poly-GT oligonucleotide tagged anti-TSH mouse monoclonal IgG was fully functional as demonstrated by the successful generation of a standard curve when it was used as binding antibody deposited on the solid-phase via biotinylated complementary poly-CA oligonucleotide coupled to avidin coated microtitre wells (see FIG. 4).

---

What is claimed is:

1. A method for determining the concentration of a plurality of analytes in a liquid sample, the method employing:
   a solid support having immobilized at discrete locations thereon a plurality of different capture agents; and
   a plurality of binding agents, each binding agent having binding sites specific for a given analyte and having a tail group adapted to bind to one of said capture agents;
   the method comprising the steps of:
   (a) contacting the liquid sample with the binding agents so that a fraction of the binding sites of each binding agent become occupied by their respective analytes;
   (b) contacting the liquid sample, either simultaneously or sequentially with step (a), with the solid support so that the binding agents become bound to their respective capture agents; and
   (c) determining a value representative of the fraction of the binding sites of a given binding agent occupied by an analyte whereby to determine the concentration of the analyte in the liquid sample
   wherein the capture agents are oligonucleotides having sequences which can hybridize to a complementary sequence on the tail group of the corresponding binding agent.

2. A method according to claim 1 wherein the oligonucleotides are between 8 and 30 bases long.

3. A method according to claim 1 wherein the binding agent is an antibody having binding sites specific for an analyte.

4. A method according to claim 1 wherein a small amount of each binding agent is used so that the ambient concentration of the analyte for which the binding agent is specific is not significantly disturbed.

5. A method according to claim 4 wherein the small amount of binding agent is less than $0.1V/K$ moles, where V is the volume of the sample and K is the effective affinity constant for the analyte binding to the binding agent.

6. A method according to claim 1 wherein each capture agent is used in excess to bind substantially all of a given binding agent.

7. A method according to claim 1 wherein the discrete locations are microspots.

8. A method according to claim 1 wherein a given capture agent is immobilized on the support at a plurality of locations so that a series of measurements of the concentration of a given analyte can be made simultaneously.

9. A method according to claim 1 wherein the value representative of the fraction of the binding sites occupied by the analyte is determined using developing agents in a competitive and/or non-competitive method, the developing agents being labelled with markers.

10. A method according to claim 9 wherein the marker are fluorescent or chemiluminescent markers.

11. A kit for determining the concentrations of a plurality of analytes in a liquid sample in a method according to claim 1, the kit comprising:
   (a) a solid substrate having attached thereto at discrete locations a plurality of different capture agents capable of specifically binding a given binding agent;
   (b) a plurality of binding agents, each binding agent having binding sites specific for a given analyte, and having a tail group adapted to bind of said capture agents; and
   (c) one or more developing agents having markers capable of binding to occupied binding agent binding sites or analyte bound to binding agent or unoccupied binding agent binding sites;
   wherein the capture agents are oligonucleotides having sequences which can hybridize to a complementary sequence on the tail group of the corresponding binding agent.

12. A kit for customizing an assay for the determination of the concentration of one or more analytes in a liquid sample, the kit comprising:
   (a) one or more tail groups, each tail group being for attachment to a binding agent;
   (b) a solid substrate having attached thereto at discrete locations a plurality of different capture agents capable of specifically binding to a tail group;
   wherein the capture agents are oligonucleotides having sequences which can hybridize to a complementary sequence on the tail group of the corresponding binding agent and the user of the assay attaches the tail groups to the binding agents, thereby providing binding agents which can be used in conjunction with the solid substrate to which the capture agents are attached in a method according to claim 1.

13. The method of claim 1 further comprising the initial step of immobilizing the plurality of different capture agents on the solid support at the discrete locations.

14. A method for determining a value representative of a fraction of binding sites of a binding agent, having binding sites specific for an analyte, that are occupied by at least one analyte present in a liquid sample, the method employing: a solid support having immobilized at discrete locations thereon a plurality of different capture agents; and a plurality of binding agents, each binding agent having binding sites specific for a given analyte and having a tail group adapted to bind to one of said capture agents, the method comprising the steps of:

(a) contacting the liquid sample with the binding agents, so that a fraction of the binding sites of each binding agent become occupied by their respective analytes;

(b) contacting the liquid sample, either simultaneously or sequentially with step (a), with the solid support so that the binding agents become bound to their respective capture agents; and (d) determining a value representative of the fraction of the binding sites of a given binding agent occupied by an analyte, wherein the capture agents are oligonucleotides having sequences that hybridize to a complementary sequence on the tail group of the corresponding binding agent.

15. A method according to claim 14, wherein the value representative of the fraction of the binding sites occupied by an analyte is determined using developing agents in a method selected from at least one of the group consisting of a competitive method and a non-competitive method, said developing agents being labelled with markers.

* * * * *